US011138734B1

(12) United States Patent
Passmore

(10) Patent No.: US 11,138,734 B1
(45) Date of Patent: Oct. 5, 2021

(54) HYPERSPECTRAL FACIAL ANALYSIS SYSTEM AND METHOD FOR PERSONALIZED HEALTH SCORING

(71) Applicant: VR Media Technology, Inc., Los Angeles, CA (US)

(72) Inventor: Charles Gregory Passmore, Austin, TX (US)

(73) Assignee: VR Media Technology, Inc., Los Angeles, CA (US)

( * ) Notice: Subject to any disclaimer, the term of this patent is extended or adjusted under 35 U.S.C. 154(b) by 0 days.

(21) Appl. No.: 17/180,681

(22) Filed: Feb. 19, 2021

(51) Int. Cl.
*G06T 7/00* (2017.01)
*A61B 5/00* (2006.01)
(Continued)

(52) U.S. Cl.
CPC .......... *G06T 7/0014* (2013.01); *A61B 5/0077* (2013.01); *A61B 5/015* (2013.01); *A61B 5/1032* (2013.01); *A61B 5/4266* (2013.01); *A61B 5/7257* (2013.01); *A61B 5/7275* (2013.01); *G16H 50/30* (2018.01); *G16H 50/70* (2018.01);
(Continued)

(58) Field of Classification Search
CPC ......... G06T 7/0014; G06T 2207/10048; G06T 2207/20048; G06T 2207/30088; G06T 2207/30201; A61B 5/0077; A61B 5/015; A61B 5/1032; A61B 5/4266;
(Continued)

(56) References Cited

U.S. PATENT DOCUMENTS

2002/0016533 A1* 2/2002 Marchitto ............ A61B 5/0066 600/310
2007/0153871 A1* 7/2007 Fraden .................. G01J 5/0022 374/121

(Continued)

OTHER PUBLICATIONS

Zhang, Lei et al. "Active polarization imaging method for latent fingerprint detection". Optical and Quantum Electronics (2018) 50: 353 (Year: 2018).*

(Continued)

*Primary Examiner* — Serkan Akar
*Assistant Examiner* — Helene Bor
(74) *Attorney, Agent, or Firm* — ARC IP Law, PC; Joseph J. Mayo

(57) ABSTRACT

A hyperspectral facial analysis system and method for personalized health scoring to assess the risk that a person has a disease. Embodiments capture images in multiple spectral bands, such as visible, infrared, and ultraviolet, and analyze these images to generate multiple health metrics, such as pallor, temperature, sweat, and chromophores. These metrics may be combined into an overall health score that may be used for screening. Image analysis may focus on the area under the eyes, where skin is thinnest. Images may be compared to a reference population to identify anomalous values, so that health scoring automatically adjusts for local conditions. Pallor may be calculated based on hue and saturation of visible light images. Temperature may be calculated based on infrared image intensity. Sweat may be calculated using cross-polarized images to identify specular highlights. Chromophores may be calculated by comparing frequency domain ultraviolet images to those of the reference population.

18 Claims, 10 Drawing Sheets
(4 of 10 Drawing Sheet(s) Filed in Color)

555 IR
553 UV 554
501 Visible
Capture Face Image of Subject in Multiple Spectral Bands
503 Locate Areas Under Eyes
504
505 Measure Under-Eye Skin in Multiple Spectra
IR 564
Visible 563
UV 565
510
511 Pallor -12
512 Temperature +6
513 Sweat -8
514 Chromophores +5
520 Combine Heath Metrics
521 522 523 -5
530 Determine Risk
Flag person for review 532 Y 531
Score < -10?
N
No further screening 533
506 Calculate Heath Metrics
544 IR
543 Visible
545 UV
540 Capture Reference Population Distributions

(51) Int. Cl.

| | |
|---|---|
| ***A61B 5/103*** | (2006.01) |
| ***A61B 5/01*** | (2006.01) |
| ***G16H 50/30*** | (2018.01) |
| ***G16H 50/70*** | (2018.01) |
| ***G16H 50/80*** | (2018.01) |

(52) U.S. Cl.
CPC ... *G16H 50/80* (2018.01); *G06T 2207/10048* (2013.01); *G06T 2207/20048* (2013.01); *G06T 2207/30088* (2013.01); *G06T 2207/30201* (2013.01)

(58) Field of Classification Search
CPC .... A61B 5/7257; A61B 5/7275; G16H 50/80; G16H 50/30; G16H 50/70
See application file for complete search history.

(56) References Cited

U.S. PATENT DOCUMENTS

2008/0294012 A1* 11/2008 Kurtz .................... A61B 5/445 600/300
2009/0318815 A1* 12/2009 Barnes ................ A61B 5/0064 600/473
2019/0192010 A1* 6/2019 Mane .................... G16H 50/30
2020/0146557 A1* 5/2020 Cheung ............... G06K 9/2018

OTHER PUBLICATIONS

Hao, Min et al. Detecting happiness using hyperspectral imaging technology. Computational Intelligence and Neuroscience, 2019, Article 1965789. https://doi.org/10.1155/2019/1965789 (Year: 2019).*
Y. Andreu-Cabedo et al., "Mirror mirror on the wall . . . An intelligent multisensory mirror for well-being self-assessment," 2015 IEEE International Conference on Multimedia and Expo (ICME), 2015, pp. 1-6, doi: 10.1109/ICME.2015.7177468 (Year: 2015).*
J. Thevenot et al. "A Survey on Computer Vision for Assistive Medical Diagnosis From Faces," in IEEE Journal of Biomedical and Health Informatics, vol. 22, No. 5, pp. 1497-1511, Sep. 2018, doi: 10.1109/JBHI.2017.2754861 (Year: 2018).*

* cited by examiner 102
103
104
105
106
101
110
111
16%
21%
15%
22%
4%
9%
78%
12%
113
114
112

210
101
Compare
202

102
101
201

106
105
103
104
301
306
315
313a
313b
314
305
303a
303b
304
320
321
111
331
332
101

320
CPU
407
GPU
405
Memory
406
Display Interface
408
Display Unit(s)
410
Secondary Memory
412
Hard Disk Drive
414
Removable Storage Drive
416
Interface
420
402
Removable Storage Unit
418
Removable Storage Unit
422
Database(s)
450
440
Network
460
Internet
Communication Interface
424
Human Interface Device(s)
430
Communication Infrastructure (Bus)

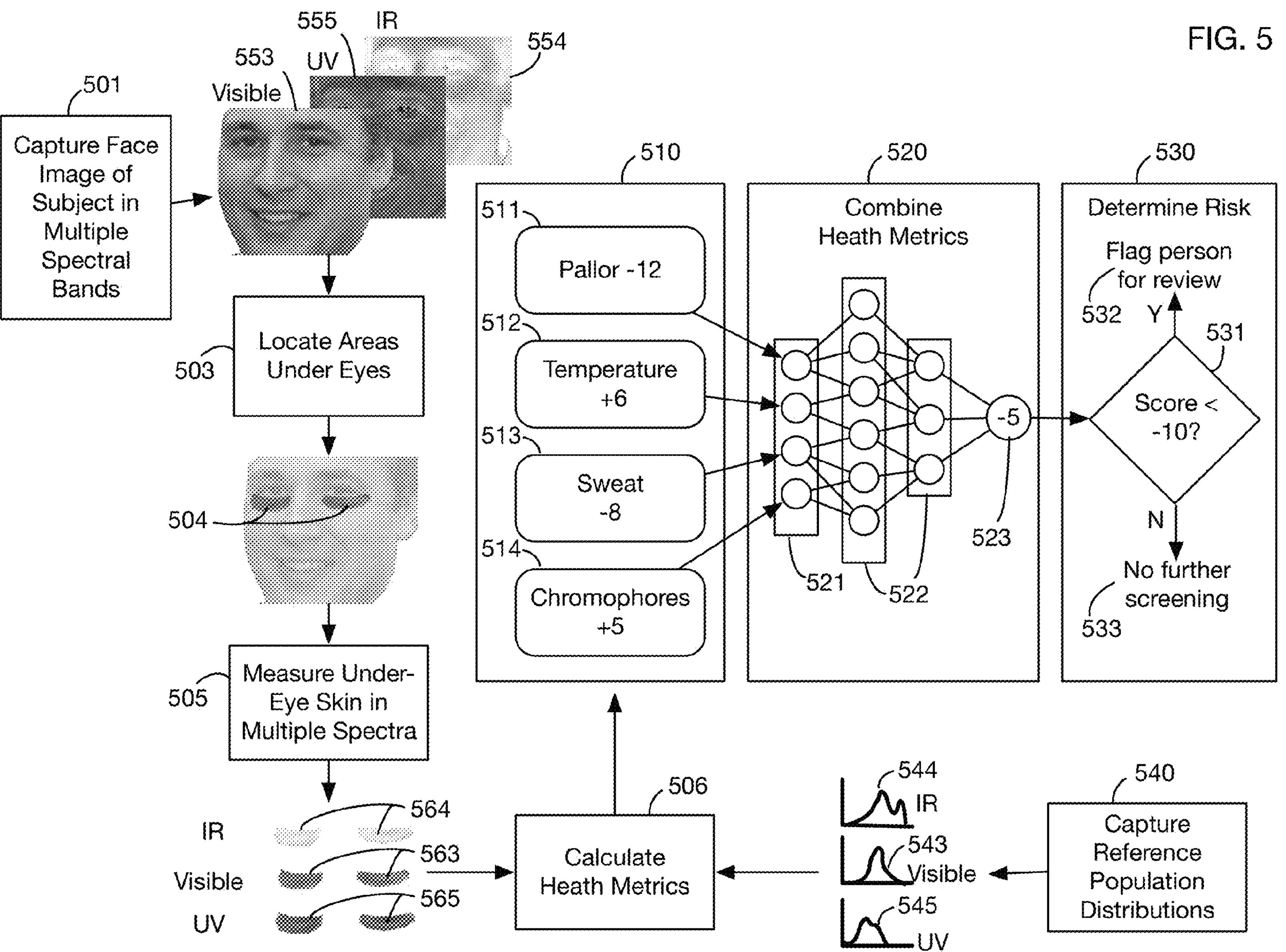
FIG. 5
501
Capture Face Image of Subject in Multiple Spectral Bands
553
Visible
555
UV
IR
554
Locate Areas Under Eyes
503
504
Measure Under-Eye Skin in Multiple Spectra
505
IR
Visible
UV
564
563
565
506
Calculate Heath Metrics
510
511
Pallor -12
512
Temperature +6
513
Sweat -8
514
Chromophores +5
520
Combine Heath Metrics
521
522
523
-5
530
Determine Risk
Flag person for review
532
Y
531
Score < -10?
N
No further screening
533
540
Capture Reference Population Distributions
544
IR
543
Visible
545
UV 1014
1015
Mean Value
1016
Chromophore +6.2
1013
Difference
1011
1012
Reference Frequency
1002
FFT
1002
FFT
565a
1001

HYPERSPECTRAL FACIAL ANALYSIS SYSTEM AND METHOD FOR PERSONALIZED HEALTH SCORING

BACKGROUND OF THE INVENTION

Field of the Invention

One or more embodiments of the invention are related to the field of health diagnostic and screening equipment. More particularly, but not by way of limitation, one or more embodiments of the invention enable a hyperspectral facial analysis system and method for personalized health scoring and in one or more embodiments a health scoring system that analyzes multispectral images of under-eye skin.

Description of the Related Art

Health screening systems that monitor a crowd and flag individuals for review are known in the art. These systems attempt to identify people with infectious diseases, such as COVID-19 or SARS, in order to stop disease spread. Known systems generally attempt to measure a person's temperature via infrared imaging. These systems have limited value because temperature alone is not an extremely reliable indicator of disease. Diseases generally affect multiple health metrics, and combining these metrics offers the potential to screen more effectively for diseases. This approach generally requires imaging in multiple spectral bands, which is not known in the art for health screening.

Another limitation of known systems is that they generally attempt to analyze the full face or even full body of a person. The inventor has found that many useful health metrics can be derived by focusing on the specific area of the face underneath the eyes; this approach is not known in the art.

For at least the limitations described above there is a need for a hyperspectral facial analysis system and method for personalized health scoring, or a health scoring system that analyzes multi spectral images of under-eye skin.

BRIEF SUMMARY OF THE INVENTION

One or more embodiments described in the specification are related to a hyperspectral facial analysis system and method for personalized health scoring, for example in some embodiments a health scoring system that analyzes multispectral images of under-eye skin. Embodiments of the invention may capture and analyze images of a person in multiple spectral bands to calculate multiple health metrics, which may then be combined into an overall health score.

One or more embodiments of the invention may have multiple imaging sensors that capture images in multiple electromagnetic spectral bands. These spectral bands may include for example, without limitation, a visible light band, an infrared light band, and an ultraviolet light band. An illustrative visible band may include wavelengths of 540 nanometers; an illustrative infrared band may include wavelengths of 700 nanometers; and an illustrative ultraviolet band may include wavelengths of 300 nanometers.

Embodiments of the invention may include a processor that receives and analyzes images from the imaging sensors. The process may receive multiple images of people in a reference population, and then compare these to images of a subject for whom a health score is calculated. The images of the reference population and of the subject may include images of people's faces; the processor may identify the under-eye regions in these facial images. The under-eye regions may for example include or correspond to the lower periorbital regions of the face. Under-eye regions of the images of the reference population may be processed to form multiple reference population distributions. The under-eye images of the subject may be compared to these reference population distributions to form multiple health metrics. The processor may then calculate a health score of the subject based on these multiple health metrics.

Illustrative health metrics that may be calculated may include for example, without limitation, pallor, temperature, sweat, and chromophores.

To calculate a pallor health metric, one or more embodiments may obtain a visible spectrum image of the face of the subject and identify the under-eye regions of this image. The system may then calculate a hue image and saturation image of these under-eye regions, and calculate a median hue and median saturation of these images. It may then calculate a relative hue and relative saturation by comparing these median hue and median saturation values to one or more of the reference population distributions. The pallor metric may then be based on the relative hue and relative saturation.

To calculate a temperature health metric, one or more embodiments may obtain an infrared spectrum image of the face of the subject and identify the under-eye regions of this image. The system may then calculate a median pixel value of these under-eye regions. It may then calculate a relative pixel value by comparing this median pixel value to one or more of the reference population distributions. The temperature metric may then be based on the relative pixel value.

To calculate a sweat health metric, one or more embodiments may obtain a pair of visible spectrum images of the face of the subject with different polarizations, and identify the under-eye regions of these images. The system may then identify the high-luminance, low-saturation pixels of these regions, and calculate a difference between the high-luminance low-saturation pixels of the two polarized images. It may then calculate a relative difference by comparing this difference to one or more of the reference populations. The sweat metric may then be based on this relative difference.

To calculate a chromophores health metric, one or more embodiments may obtain an ultraviolet image of the face of the subject, and identify the under-eye regions. The system may calculate a Fourier transform of these regions and calculate a difference between this transformed image and a reference Fourier transform based on one or more of the reference population distributions. The chromophores metric may then be based on difference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other aspects, features and advantages of the invention will be more apparent from the following more particular description thereof, presented in conjunction with the following drawings wherein:

FIG. 5 shows an illustrative flowchart of processing steps to capture data and process the data to calculate health measures and a combined health score.

DETAILED DESCRIPTION OF THE INVENTION

A hyperspectral facial analysis system and method for personalized health scoring or in some embodiments a health scoring system that analyzes multispectral images of under-eye skin will now be described. In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1:
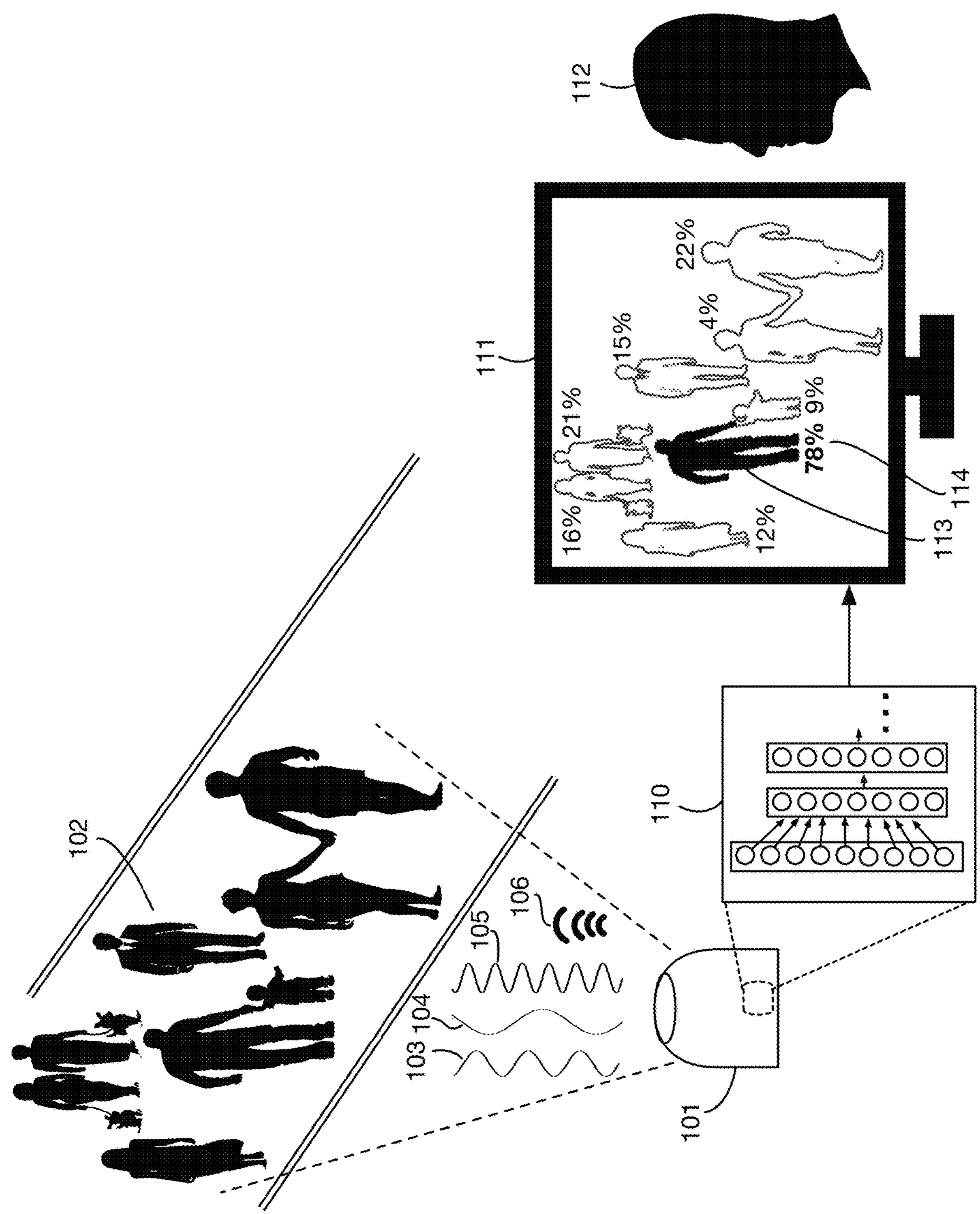
FIG. 1 shows an illustrative embodiment of a health scoring system that may be used to screen people in a public space for health conditions, such as infectious diseases.

FIG. 1 shows an illustrative application of a health scoring system 101. This health scoring system may for example monitor people 102 who may pass through an area such as an airport, office, or arena. The system may identify persons who may show some signs of certain health conditions, such as infectious diseases. One use of the health scoring system may be to flag people who appear to be at elevated risk for one or more diseases, so that these people can be intercepted and tested or interviewed further. Illustrative applications may be for example screening people for signs of COVID-19, SARS, Ebola, influenza, or other conditions that may be easily transmitted and may pose a considerable public health risk.

Illustrative health scoring system 101 may monitor the crowd 102 using multiple channels. Each channel may monitor a specific physical signal, such as electromagnetic waves in selected spectral bands. Other potential signals that may be monitored may include for example, without limitation, audio, vibration, temperature, weight, and size or shape. In one or more embodiments, health scoring system 101 may monitor any desired combination of physical signals in order to assess the health condition of people it observes. A potential benefit of using multiple channels is that classification accuracy can be higher than that of systems that monitor a single channel (such as temperature); in addition, combining multiple channels reduces the effect of noise in any single channel, which can be significant.

Illustrative system 101 monitors channels 103, 104, 105, and 106. Channel 103 may be for example a visible light channel (monitored for example with a visible light camera); channel 104 may be an infrared light channel; channel 105 may be an ultraviolet light channel; and channel 106 may be a depth channel. The depth channel may for example use LIDAR, structured light, ultrasound, or stereo vision to determine the distance to a person or to any of the person's features. These channels are illustrative; one or more embodiments may monitor any desired combination of physical signals.

System 101 may contain or communicate with one or more processors that perform data analyses 110 to map the raw data from the monitored channels into a health score for each monitored person. These analyses may use any desired signal processing techniques or algorithms. The final result of this processing may be a combined health score for each monitored individual. This health score may be on any scale; it may be continuous or discrete (such as a classification of individuals into risk strata). The health score may be transmitted from system 101 to any other systems, such as an operator computer 111. An operator 112 may for example view the results of the health scoring system to determine whether specific individuals should be stopped for further screening. In the example shown in FIG. 1, the health score is expressed as a risk percentage, and persons with a risk above 70% are highlighted on the operator's screen; thus person 113 is highlighted for further screening because his associated health score 114 exceeds the threshold.

In one or more embodiments, detection of an anomalous health score may be based on comparing a subject's health metrics to those of a reference population, rather than comparing to some absolute standard. This approach has two potential benefits. First, it may obviate the need to calibrate sensors against some absolute reference. Second, it may automatically adapt to different local conditions of the environment or the reference population. As an example, the normal skin temperature for a person in Las Vegas in the summer may be considerably higher than the normal skin temperature for a person in Sweden in the winter. By comparing a person's skin temperature to the typical values for the reference population, the system may more effectively screen for unusual health conditions.

Figure 2B:
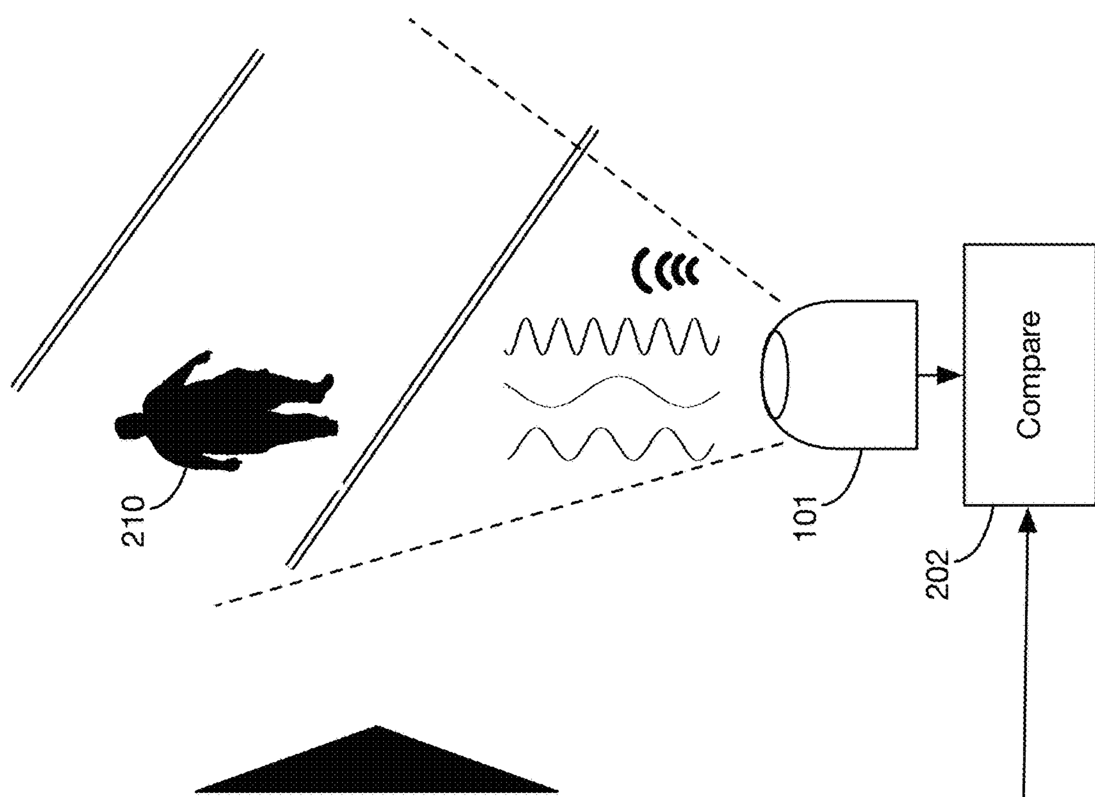
FIG. 2B shows applying this system to screening of a new individual by comparing that individual's measurements to this database.
Figure 2A:
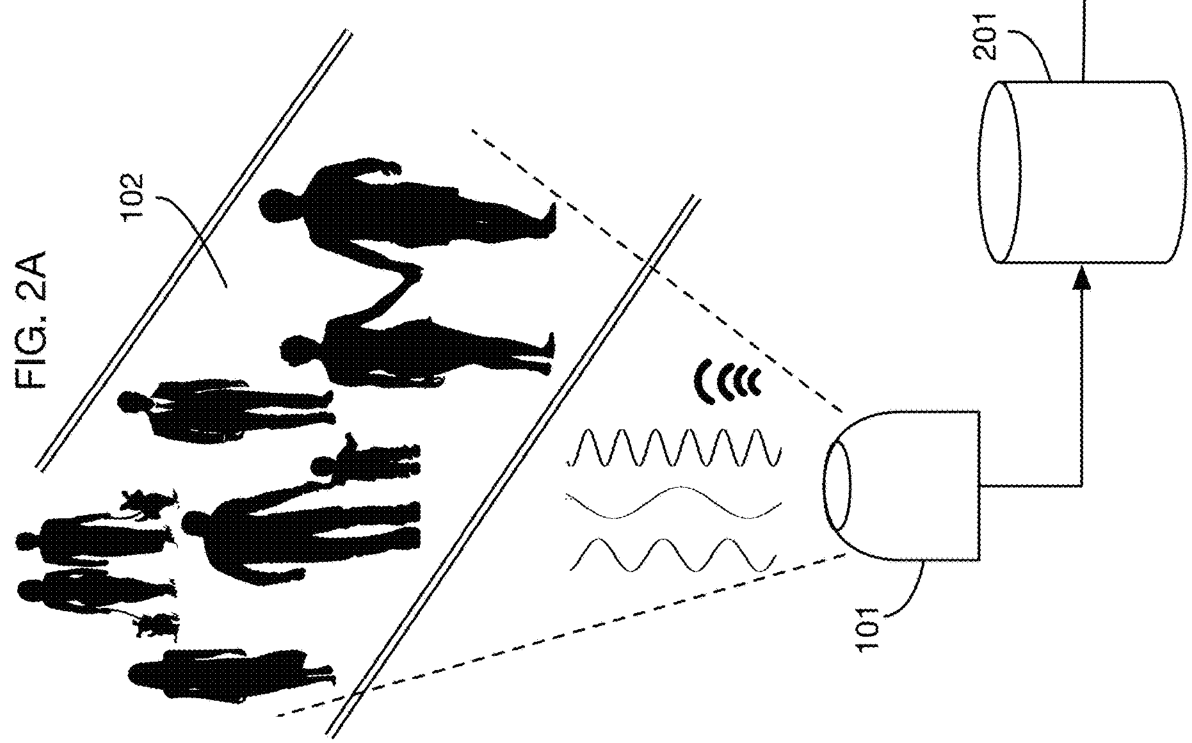
FIG. 2A shows the system of FIG. 1 collecting data from a reference population to develop a database of typical values that may be used to identify anomalies.

FIGS. 2A and 2B illustrate this approach of comparing a subject's measurements to those of the reference population. In FIG. 2A, system 101 learns the typical values or distribution of the crowd 102, and stores this data in database 201. This crowd 102 forms the reference population. In FIG. 2B, a new subject 210 comes into view and the system 101 executes a comparison 202 of this person's data to the database 201. Data in database 201 may be updated continuously for example as a running average, or periodically in a recalibration phase, so that the reference population is modified over time to reflect current conditions.

Figure 3:
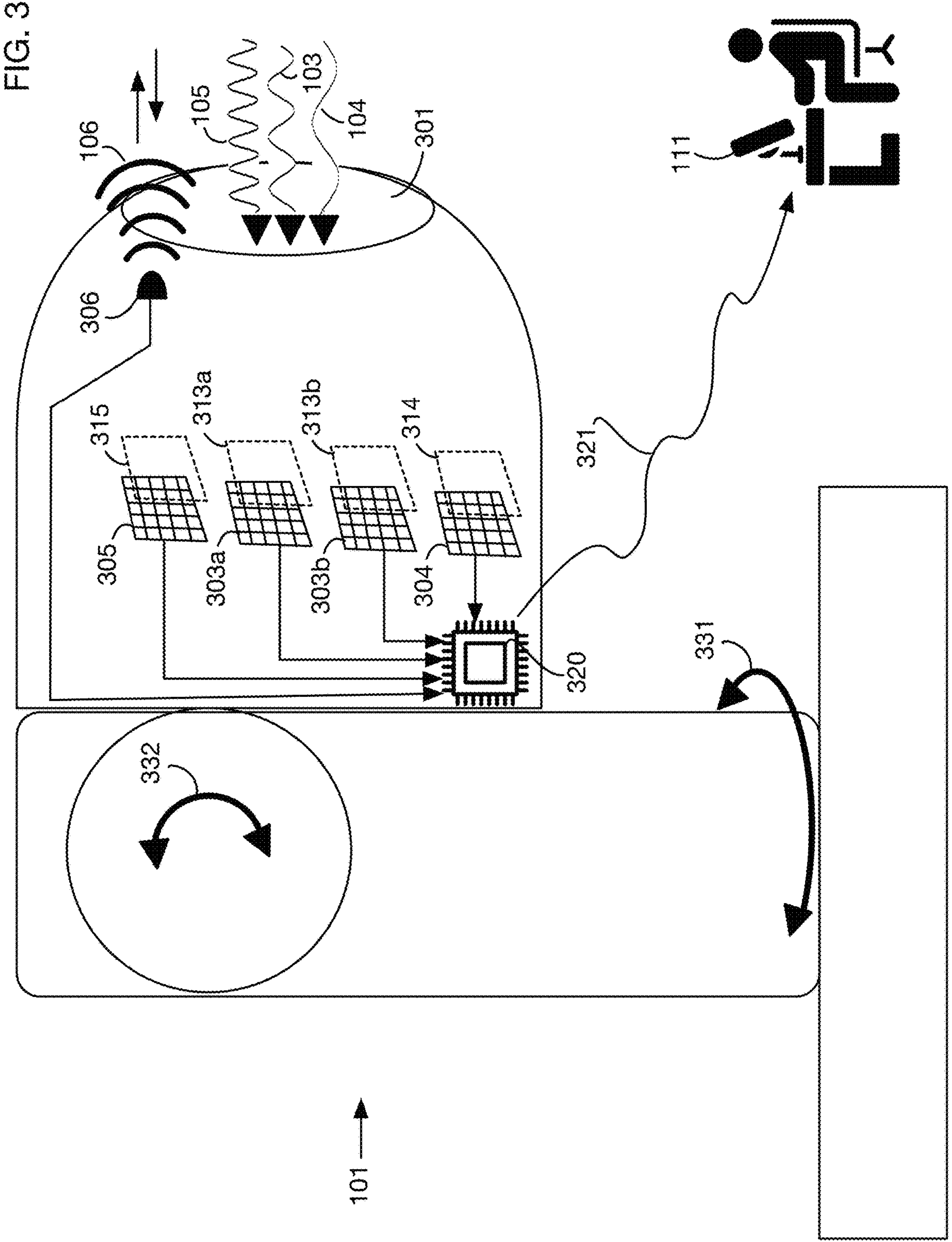
FIG. 3 shows illustrative components of a health scoring system, including sensors that capture images in multiple spectra, a processor that processes sensor data, and potentially actuators that can aim or reposition the system.

FIG. 3 shows an architecture diagram of an illustrative embodiment of health scoring system 101. This embodiment has a housing with an aperture 301, which collects physical signals 103, 104, 105, and 106. The housing contains sensor arrays 303*a* and 303*b*, 304, and 305, which measure signals 103, 104, and 105, respectively. Each sensor array may be coupled to one or more filters that for example select desired wavelengths or other signal characteristics. For example, filter or filters 314 may select an infrared wavelength band centered at approximately 700 nm (with a width for example of approximately 100 nm). Filter or filters 315 may select an ultraviolet wavelength band centered at approximately 300 nm (with a width for example of approximately 100 nm). Filters 313*a* and 313*b* may select a visible light band centered at approximately 540 nm; these two filters may be cross-polarized, in order to select different polarizations for sensors 303*a* and 303*b*. These sensors, filters, and wavelengths are illustrative; one or more embodiments may collect any types of physical signals in any band or bands of wavelengths or other characteristics.

System 101 also contains a depth sensor 306, which may be for example a LIDAR that both emits and collects light to determine the distance to a subject and to the subject's features.

Data from sensors 303*a*, 303*b*, 304, 305, and 306 may be transmitted to one or more processors 320 for analysis. Processor 320 may be integrated into or coupled to system 101, or it may be a separate unit and the system may transmit data to this processor or processors over any type of link or network. Processor 320 may be for example, without limitation, a microprocessor, a microcontroller, a CPU, a GPU, an ASIC, a computer, a desktop computer, a laptop computer, a notebook computer, a tablet computer, a smartphone, a server, or a network of any of these devices.

Processor 320 may communicate with other systems such as operator workstation 111, over any network connection such as a wireless or wired link 321. In one or more embodiments, data analysis may be shared between processor 320 and these external systems such as workstation 111. Data analysis may be partitioned among processors in any desired manner.

System 101 also contains a pan actuator 331 and a tilt actuator 332, so that aperture 301 can be aimed at any person or group of people in an area that is being monitored. In one or more embodiments, the system may also contain zoom or telescoping features that allow closeup views of specific subjects of interest.

Figure 4:
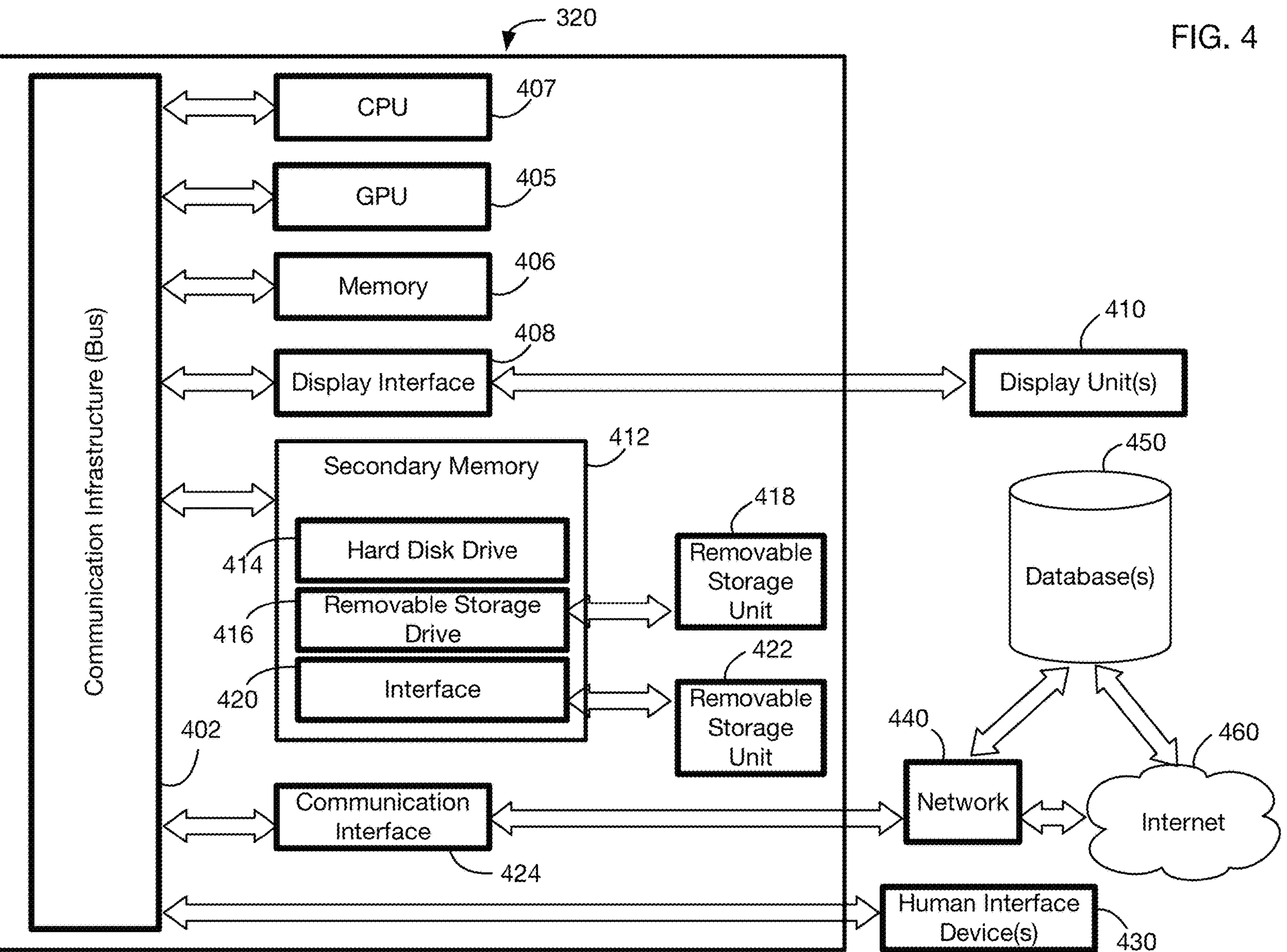
FIG. 4 illustrative hardware components of a system processor for the embodiment of FIG. 3.

FIG. 4 shows an embodiment of exemplary computer 400 that may be utilized in, by, or as any component in the system. For example, computer 400 or any of its components may be health scoring system processor 320 or operator workstation 111. In one or more embodiments, computer 400 may be a network of computers, each of which may have any or all of the components shown in FIG. 4. In one or more embodiments, computer or computers 400 may also be utilized to implement any function in the system, i.e., any step or act or function that executes in any computer or server or engine in the system. Computer 400 may include processor CPU 407 that executes software instructions specifically tailored to the respective functions of embodiments of the invention. The software instructions, otherwise known as computer program instructions, may reside within memory 406. Computer 400 may include processor GPU 405, which may execute graphics instructions or other instructions for highly parallel operations, for example. GPU program instructions may also reside within memory 406. Computer 400 may include display interface 408, which may drive display unit or units 410 of any computer in the system as desired. Some computers 400 may or may not utilize a display. Computer 400 may include communication interface 424, which may include wireless or wired communications hardware protocol chips. In one or more embodiments of the invention communication interface 424 may include telephonic and/or data communications hardware. In one or more embodiments communication interface 424 may include a Wi-Fi™ and/or BLUETOOTH™ wireless communications interface. Any wireless network protocol or type may be utilized in embodiments of the invention. CPU 407, GPU 405, memory 406, display interface 408, communication interface 424, human interface devices 430, secondary memory 412, such as hard disk 414, removable storage 416, secondary memory interface 420 and removable storage units 418 and 422 may communicate with one another over communication infrastructure 402, which is commonly known as a "bus". Communications interface 424 may communicate over any wired or wireless medium that allows for communication with other wired or wireless devices over network 440. Network 440 may communicate with Internet 460 and/or database or databases 450. Database 450 may be utilized to implement any database described herein.

We now describe illustrative health measures that may be calculated by one or more embodiments of health scoring system 101. These specific measures are illustrative; one or more embodiments may measure any physical signals and calculate any desired health measures from these signals. One or more embodiments may use a subset or a superset of any of the health measures described below.

FIG. 5 shows a flowchart of an illustrative sequence of steps to calculate and combine four illustrative health measures. In this example, the health measures are based on multi-spectral images of the area of a person's face underneath the eyes. Use of the under-eye region for analysis of a person's health provides at least two benefits: First, the skin in the region underneath the eyes the skin is typically thin, so analysis of this region (particularly with multiple spectra outside the visible range) may reveal features such as blood perfusion or other physiological features. Second, the under-eye region is typically not covered by either masks or headwear, so it is available for analysis under most situations.

In step 501, the system may capture images of all or part of a subject's face, possibly in multiple spectral wavelengths. For example, this step yield images such as image 553 in the visible spectrum, image 554 in the infrared spectrum, and image 555 in the ultraviolet spectrum. In step 503, these images are input into a process that locates the desired areas under the eyes 504. In one or more embodiments, there may be other inputs into this locating step, such as a depth channel for example. Step 505 then generates under-eye images or measurements of these under-eye areas in multiple spectra, yielding for example visible spectrum under-eye measurements 563, infrared under-eye measurements 564, and ultraviolet under-eye measurements 565. These measurements may then be input into step 506 that calculates one or more health metrics from the under-eye measurements. FIG. 5 shows four illustrative health metrics 510 that may be calculated from the under-eye measurements. These metrics are illustrative; one or more embodiments may use any health metrics or combination of health metrics, or may use a subset or superset of the metrics shown in FIG. 5. The illustrative health metrics 510 are pallor 511, temperature 512, sweat 513, and chromophores 514. Each of these metrics may provide indications of the health of the subject. Illustrative examples of calculating each of these metrics are described below with respect to FIGS. 7 through 10.

As described above with respect to FIG. 2, one or more embodiments may calculate health metrics relative to a reference population, rather than (or in addition to) relative to an absolute standard. Therefore the distributions 543, 544, and 545 of reference population under-eye skin measurements (in visible, infrared, and ultraviolet spectra, respectively) may also be input into the calculation step 506; these distributions may be collected in step 540 that monitors or samples the reference population.

In step 520, the health metrics 520 are combined into an aggregate health score 523. These metrics may be combined in any desired manner. FIG. 5 illustrates use of a neural network to map the health metrics 510 into an aggregate health score 523. For example, the input layer of the neural network 521 receives the four individual health metrics, the hidden layers 522 process the inputs, and output layer 523 provides the combined health score. One or more embodiments may use any method or algorithm to combine multiple metrics into an aggregate health score.

In step 530, the health score 523 is used to determine whether the subject should be flagged for addition review 532, or whether no further screening is necessary 533. An illustrative method to determine whether to flag an individual is to perform comparison 531 of the health score 523 to a threshold value.

Figure 6A:
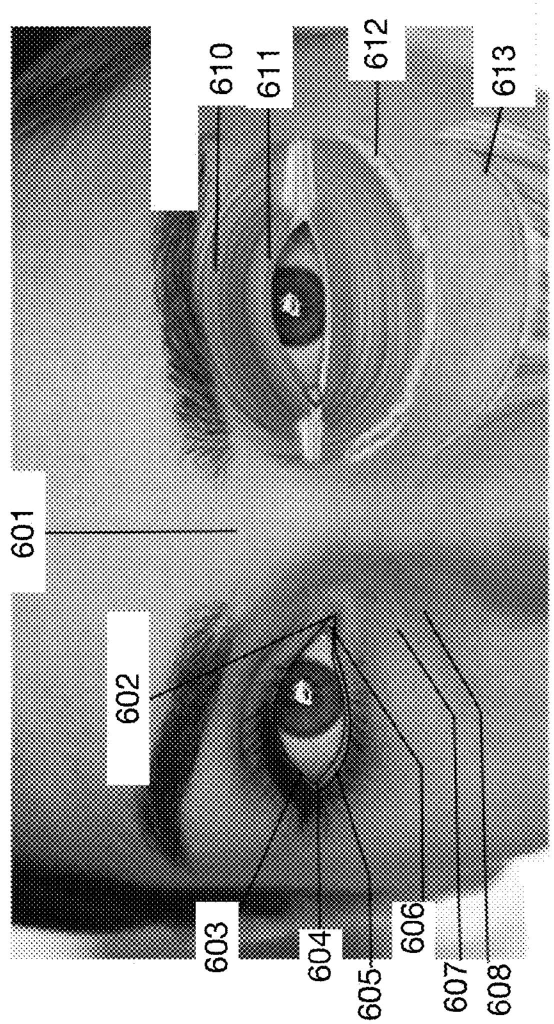
FIGS. 6A and 6B show reference locations and distances on a human face that may be used to identify the under-eye region of interest for calculation of health measures.
Figure 6B:
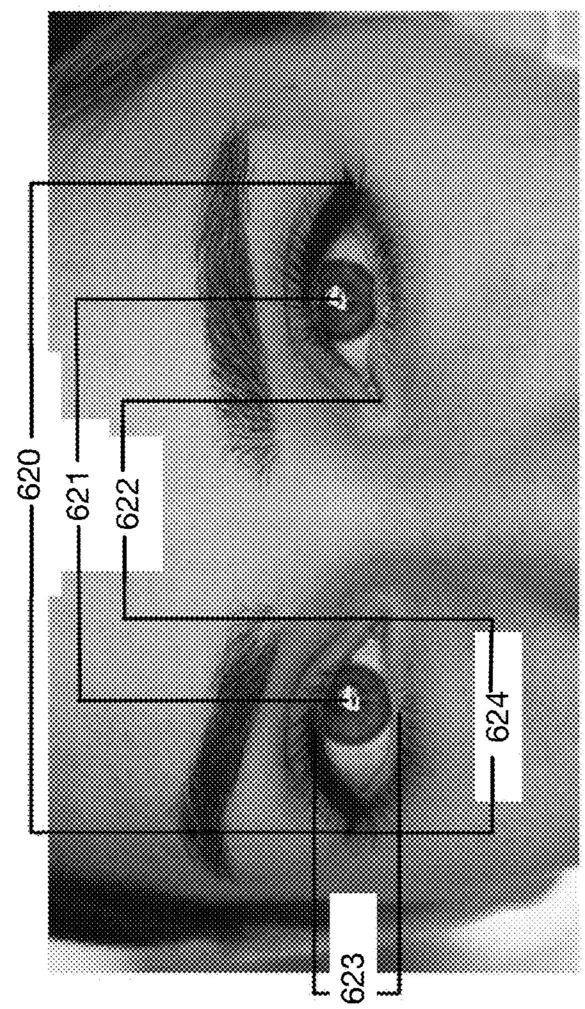

We now describe a method that may be used in one or more embodiments to perform step 503—locating the areas under the eyes in facial images. This step may be applied to images of the reference population and to images of the subject for whom a health score is calculated. The following description refers to FIGS. 6A and 6B, which identify facial landmarks and distances, respectively. The area of interest under the eyes is generally referred to as the lower Periorbital subunits. Identification of this region may be accomplished after image perspective rectification. First the eyes may be locating roughly and then a set of metrics may be calculated to refine the periorbital locations and extents as follows.

The first marker is the identification of lateral canthus 604 and the medial canthus 602 to determine the length 624 of the palpebral fissure. This may be performed in HLS color space. A min/max calculation in the face may then determine the maximum length axis (delta) in each color channel; hue, luminance and saturation. This accounts for differences in skin tone and color. The HLS channel with the greatest delta may then be used. The sclera may be segmented in the thermal channel, because the sclera is flat and unshaded in thermography. Once segmented, corner detection may be used to locate each canthus. These may then then sorted horizontally to yield the lateral and medial canthus for each eye.

Blepharon Location: A next step is to outline the blepharon. This may also be accomplished using thermography, because the iris, which normally interferes with eye segmentation also remains flat in thermographic imagery. Once the eye is removed, the edge may be amplified using a vertical gradient detector Additional confidence can be obtained, when sufficient imaging resolution is available, by identifying and locating the lacrimal puncha 606. The puncha becomes an anchor along the blepharon, along with the two canthi. These three points are enough to create a spline, but a vertical gradient detector may be used to create additional points along the blepharon. This may be accomplished by windowing the eye, thresholding the gradient image and taking the bottom XY value along each vertical scalene. Values which outliers are excluded if greater than 1.5 times the Interquartile range, although other methods may be used. Missing points along the blepharon are not a problem since outlining may use splines, allowing representation of the boundary in a scale invariant manner without need for spacing homogeneity.

Glabella Location: Once the respective palpebral fissure lengths are determined, the glabella 601 can be located by following the nasal ridge upwards to the upper orbital between the eyebrows. Because cosmetic plucking can alter the eyebrow profile, the flattening of the upper nasal bridge can be used to assist in verification of the appropriate location, which is generally centered on the inner canthal distance 622. To perform this, we stereoscopy or Lidar may be used to measure the nasal ridge and subsequent top end flattening. Flatness can be determined by calculating a cubic polynomial regression and seeking a minimum threshold value in the cubic coefficient.

Zygomatic Cutaneous Ligament Location: The top of the modal cheek compartment, which lies outside the periorbital subunits, can be located by determining the location of the lower zygomatic cutaneous ligament 613. There is controversy regarding the medial ligament and the orbicularis oculi muscle may be directly attached to the bone along the tear trough 607. That being said, the theoretical location of the zygomatic cutaneous ligament 613 may be used as a critical marker. This can be identified using a depth field and locating the tear trough 607 through the watershed algorithm. The tear trough may not be the only marker because the relationship between the tear trough 607 and the nasojugal groove 608 change with age, often caused by herniation of the tear trough by orbital fat. As such, the zygomatic cutaneous ligament 613 may be located by treating both the tear trough and nasojugal groove as one.

Palpebromalar Groove Location: Unlike the zygomatic cutaneous ligament, the palpebromalar groove runs roughly parallel to the blepharon. The depth channel and the watershed algorithm may be used to identify this groove's location. A ridge, the mid-cheek groove, runs below the palpebromalar groove and serves as a convenient demarcation.

Palsy: Because image rectification may contain rotational error, a vector may be extended across the two inner canthal points and another vector across the outer canthal points. The dot product of these two vectors separates head rotation from palsy. Further confidence is obtained by calculating the orthogonal nose ridge vector and comparing the dot products with our two canthal vectors. The inner vector should exhibit a 90° angle with the nose ridge, while the out canthal vector will illuminate asymmetry, indicative of palsy.

Lower Periorbital Region Location: The lower periorbital regions are upper bounded by the glabella, but offset by palsy (or other causes of asymmetry). The horizontal bounds are defined by the palpebral fissure length 624. The lower bounds are defined by the intersection of the medial zygomatic cutaneous ligament 613 and the palpebromalar groove, running to the lateral edge of the palpebromalar groove, horizontally clamped by the lateral extent and length of the palpebral fissure.

Figure 7:
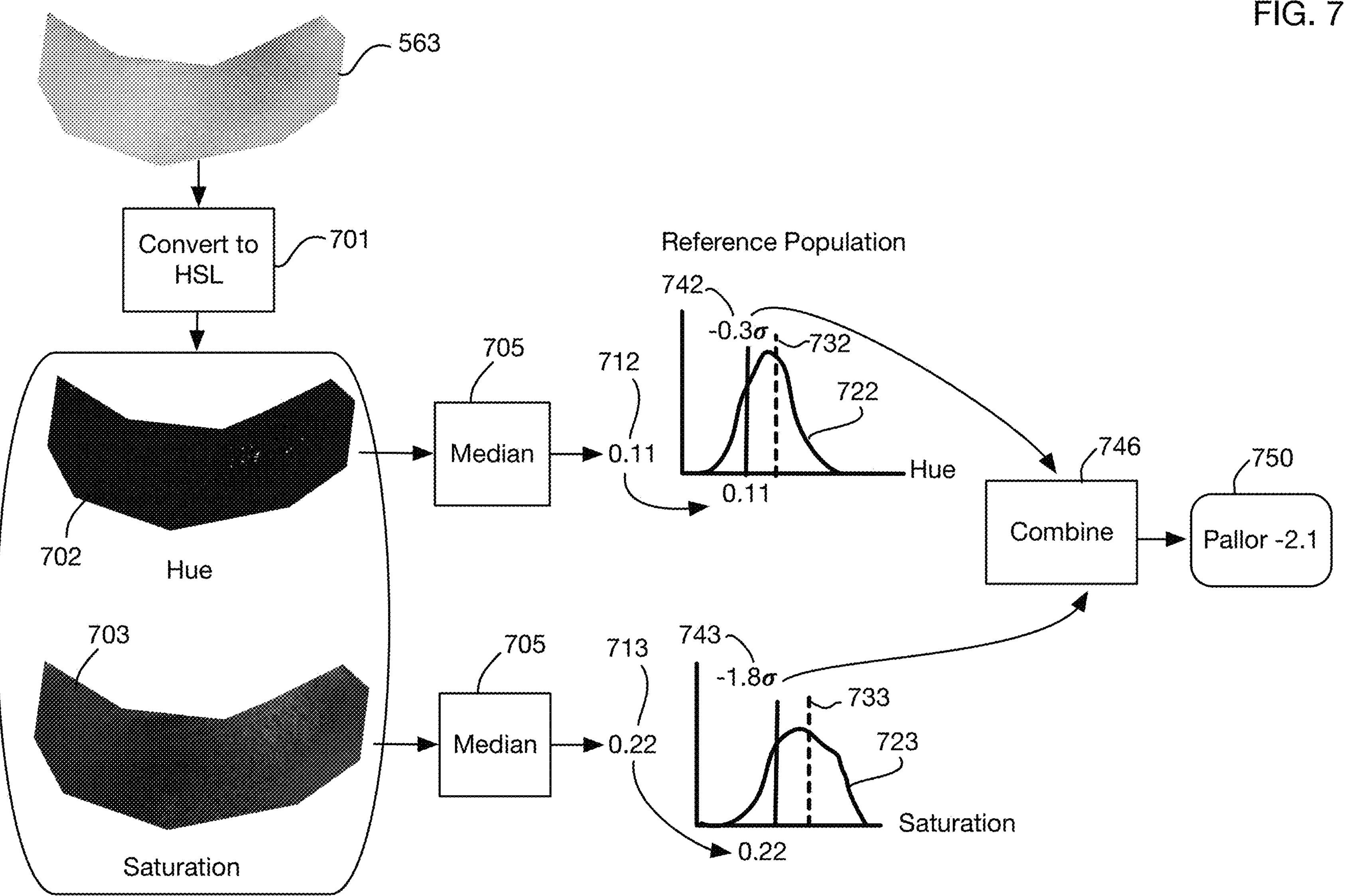
FIG. 7 illustrates calculation of a pallor health measure.

Turning now to illustrative calculations of health metrics 510 shown in FIG. 5, FIG. 7 shows an illustrative method for calculating pallor that may be used in one or more embodiments. Pallor may be indicative of health in part because it may reflect hypoxia, for example, as an indicator of oxygen deficiency. This is useful as an indicator of fitness and can point to respiratory illness and anemia. To measure pallor, a visible spectrum image 563 of the under-eye areas of a face may be first converted in step 701 to the HSL color space. (For ease of illustration, FIG. 7 shows the image of a single eye; in practice both eyes may be used.) To do color comparisons, we must move out of the RGB space because luminance is coupled with each color channel. Pallor is expressed in color, not luminance. Removing luminance from the image may normalize for ethnic skin differences, for example, which are primarily differences in luminance. We can use the linear HLS space or the nonlinear LAB space. Research exists on using LAB space for pallor mortis, but the inventors have found that LAB is not optimal because LAB color shifts hue when luminance is modified. This occurs because LAB is designed to mimic human perception, but this inter-coupling of channels makes LAB of limited use. LAB is also limited in its valid luminance. Thus, we convert RGB to HLS to decouple luminance to obtain hue 702 and saturation 703 for the under-eye regions.

A median operator 705 may be applied to the under-eye pixel values in the hue and saturation channels 702 and 703, respectively, and normalized to the range 0 to 1, to form median hue 712 and median saturation 713. These medians may then be compared to the reference population distributions 722 and 723 for hue and saturation, respectively. For example, a hue measure 742 may be calculated as the number of standard deviations the hue median 712 deviates from the median 732 of the population distribution, and similarly a saturation measure 743 may be calculated as the number of standard deviations the saturation median 713 deviates from the median 733 of the population distribution. These normalized deviation scores 742 and 743 may then be combined in step 746 to yield an aggregate pallor health score 750. They may be combined using any weights or algorithm; FIG. 7 shows a simple combination method that sums the two deviations to obtain a pallor score.

Figure 8:
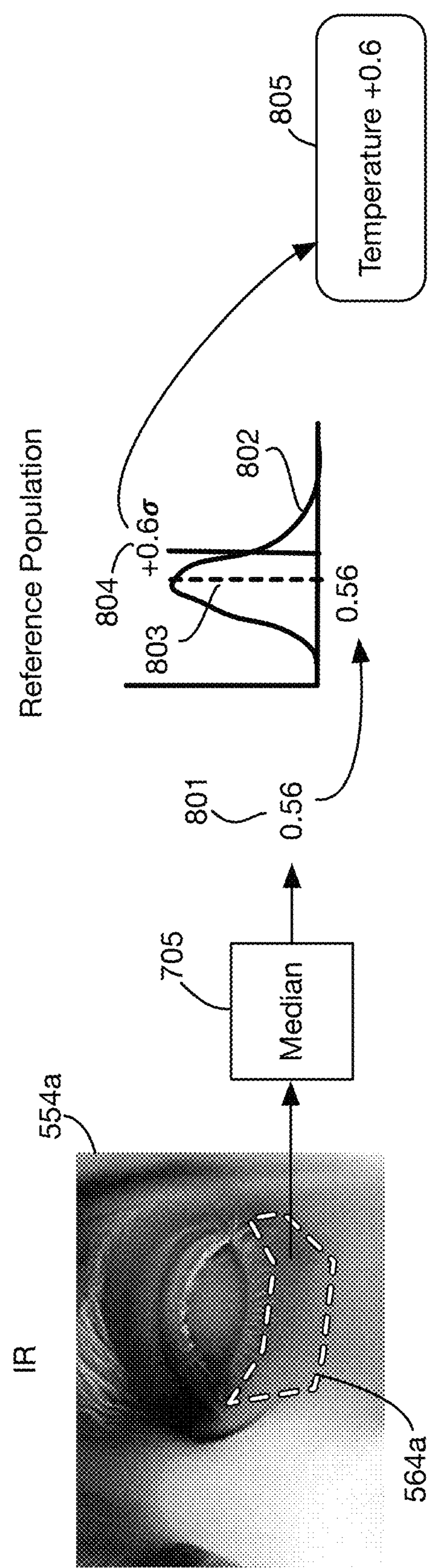
FIG. 8 illustrates calculation of a temperature health measure.

FIG. 8 shows an illustrative method that may be used to calculate a temperature metric by analyzing an infrared image 554*a* of a subject's face. The under-eye areas 564*a* may be obtained (as described above) and a median filter 705 may be applied to the pixel in these areas to obtain a median value 801 (which may for example be normalized to the range 0 to 1). This median may then be compared to the reference population distribution 802 of under-eye infrared pixel values. A temperature measure 805 may be calculated as the number of standard deviations 804 the median 801 deviates from the median 803 of the population distribution 802.

Figure 9:
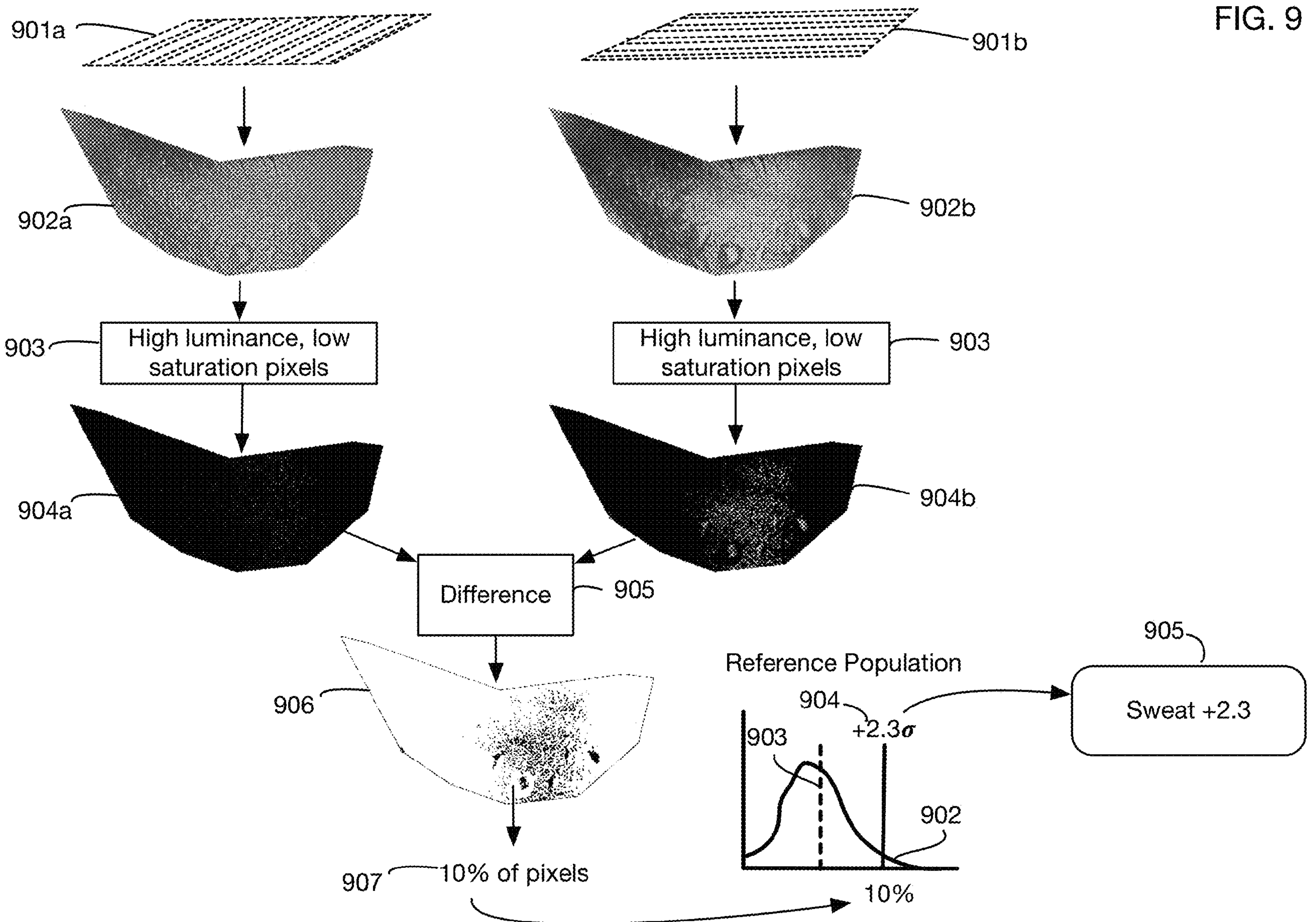
FIG. 9 illustrates calculation of a sweat health measure.

FIG. 9 shows an illustrative method that may be used to calculate a sweat metric, which indicates how much the subject is sweating. The amount of sweating may be correlated with other health factors such as fever or stress. The method shown in FIG. 9 uses two opposite cross polarized channels to identify the specular highlights of moisture. A visible light channel may be measured by two sensors, which may be genlocked for example, with cross polarized filters 901*a* and 901*b* in front of each sensor to select a polarization. This yields under-eye polarized images 902*a* and 902*b*, respectively. (Again, for ease of illustration only a single eye is shown.) In step 903, the high luminance, low saturation pixels are selected from images 902*a* and 902*b*, yielding masks 904*a* and 904*b*, respectively. These masks are then differenced in operation 905, yielding the difference mask 906. (For ease of illustration, pixels with a nonzero difference are shown as black in image 906.) The nonzero pixels in image 906 correspond to specular highlights. A count of the number of difference pixels 907 (expressed here as a fraction of the total number of pixels) may then be used to develop a sweat metric. This count 907 may be compared to the reference population distribution 902 of the number of difference pixels. A sweat measure 905 may be calculated as the number of standard deviations 904 the count 907 deviates from the median 903 of the population distribution 902.

Figure 10:
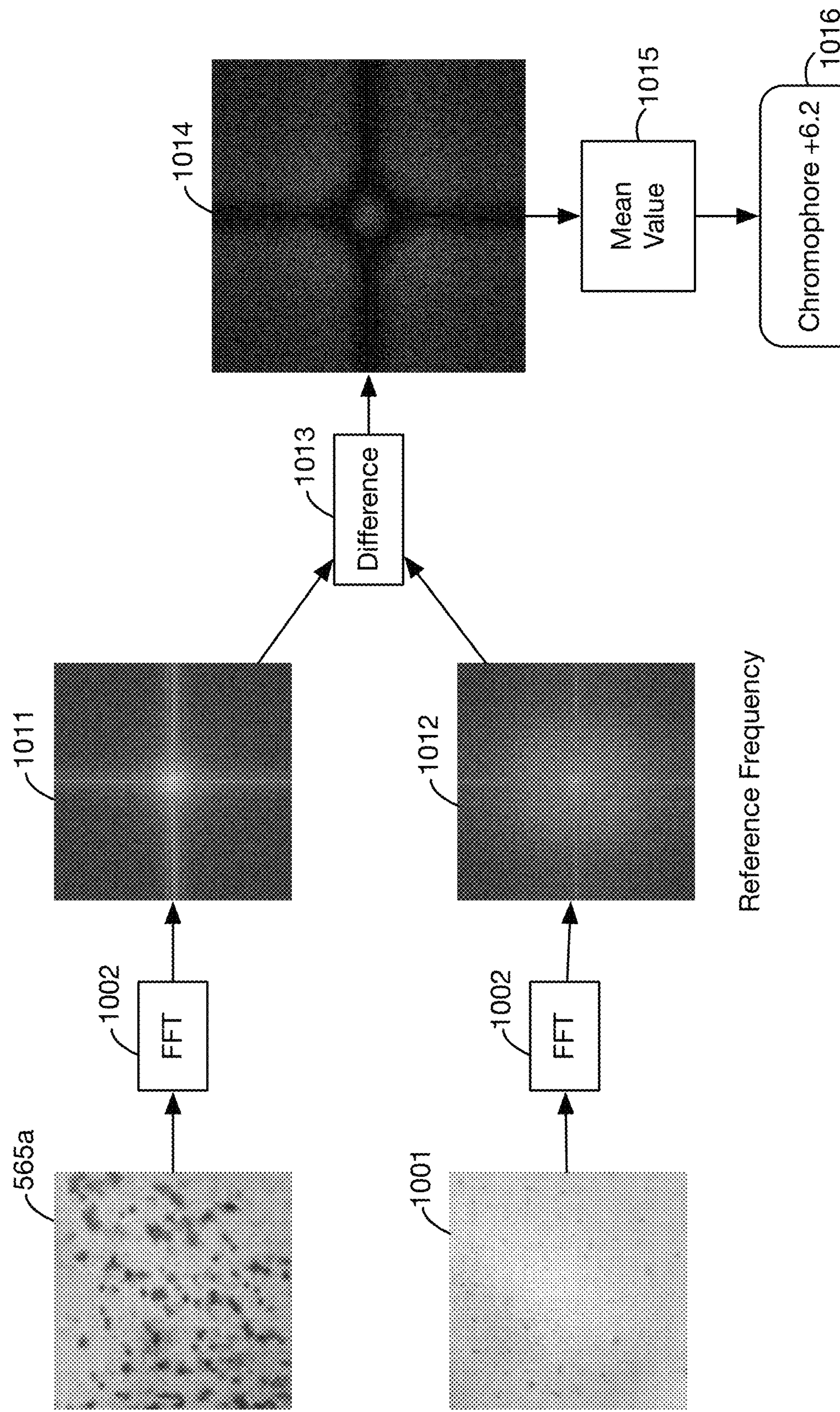
FIG. 10 illustrates calculation of a chromophores health measure.

FIG. 10 shows an illustrative method that may be used to calculate a chromophore score. This score may for example reflect the frequency or size of chromophores in the subject's facial skin, which may be indicative of various health conditions. Chromophores may be measured in the ultraviolet spectrum. The method shown in FIG. 10 analyzes the ultraviolet facial image in the frequency domain. A small patch of facial skin 565*a* is shown for illustration; the method may be applied to the entire under-eye skin area or to any desired portion of the face. This patch 565*a* is the image of a skin patch in the ultraviolet channel. A fast Fourier transform 1002 is applied to this image to obtain 2D frequency spectrum 1011, shown as the log of the modulus of the FFT. A similar transform 1002 may be applied to an average or typical image 1001 obtained from the reference population to obtain a reference frequency spectrum 1012. These frequency spectra 1011 and 1012 are subtracted in operation 1013, yielding a difference 1014. The mean value 1015 of the pixels in the frequency difference 1014 may be used to calculate a chromophore score 1016.

While the invention herein disclosed has been described by means of specific embodiments and applications thereof, numerous modifications and variations could be made thereto by those skilled in the art without departing from the scope of the invention set forth in the claims.

What is claimed is:

1. A hyperspectral facial analysis system for personalized health scoring comprising:
- a plurality of imaging sensors configured to capture images in a plurality of electromagnetic spectral bands; and,
- a processor coupled to said plurality of imaging sensors and configured to
  - receive a multiplicity of person images from said plurality of imaging sensors, wherein each person image of said multiplicity of person images comprises a face of a corresponding person of a reference population;
  - identify under-eye regions of said each person image;
  - analyze said under-eye regions corresponding to said multiplicity of person images to form a plurality of reference population distributions;
  - receive a plurality of subject images from said plurality of imaging sensors, wherein each subject image of said plurality of subject images comprises a face of a subject;
  - identify under-eye regions of said each subject image;
  - calculate a plurality of health metrics of said subject based on comparisons of only said under-eye regions of said each subject image to one or more of said plurality of reference population distributions; and,
  - calculate a health score of said subject based on said plurality of health metrics of said subject.

2. The system of claim 1, wherein said plurality of electromagnetic spectral bands comprise
- a visible spectrum band;
- an ultraviolet spectrum band; and,
- an infrared spectrum band.

3. The system of claim 2, wherein
- said visible spectrum band comprises 540 nanometers;
- said infrared spectrum band comprises 700 nanometers; and,
- said ultraviolet spectrum band comprises 300 nanometers.

4. The system of claim 1, wherein
- said under-eye regions of said each person image comprise lower periorbital regions of said face of said corresponding person; and,
- said under-eye regions of said each subject image comprise lower periorbital regions of said face of said subject.

5. The system of claim 1, wherein
- said plurality of health metrics of said subject comprise pallor.

6. The system of claim 5, wherein said plurality of subject images comprise a visible spectrum image of said face of said subject; and, said calculate said plurality of health metrics of said subject comprises identify under-eye regions of said visible spectrum image;

calculate a hue image of said under-eye regions of said visible spectrum image;

calculate a saturation image of said under-eye regions of said visible spectrum image;

calculate a median hue of said hue image;

calculate a median saturation of said saturation image;

calculate a relative hue based on a comparison of said median hue to said one or more of said plurality of reference population distributions;

calculate a relative saturation based on a comparison of said median saturation to said one or more of said plurality of reference population distributions; and, calculate said pallor based on said relative hue and said relative saturation.

7. The system of claim 1, wherein said plurality of health metrics of said subject comprise temperature.

8. The system of claim 7, wherein said plurality of subject images comprise an infrared spectrum image of said face of said subject; and, said calculate said plurality of health metrics of said subject comprises identify under-eye regions of said infrared spectrum image;

calculate a median pixel value of said under-eye regions of said infrared spectrum image;

calculate a relative pixel value based on a comparison of said median pixel value to said one or more of said plurality of reference population distributions; and, calculate said temperature based on said relative pixel value.

9. The system of claim 1, wherein said plurality of health metrics of said subject comprise sweat.

10. The system of claim 9, wherein said plurality of subject images comprise a pair of visible spectrum images of said face of said subject with different polarizations; and, said calculate said plurality of health metrics of said subject comprises identify under-eye regions of said pair of visible spectrum images;

identify high-luminance, low-saturation pixels of said under-eye regions of said pair of visible spectrum images;

calculate a difference between said high-luminance, low-saturation pixels of under-eye regions of a first image of said pair of visible spectrum images, and said high-luminance, low-saturation pixels of under-eye regions of a second image of said pair of visible spectrum images;

calculate a relative difference based on a comparison of said difference to said one or more of said plurality of reference population distributions;

calculate said sweat based on said relative difference.

11. The system of claim 1, wherein said plurality of health metrics of said subject comprise chromophores.

12. The system of claim 11, wherein said plurality of subject images comprise an ultraviolet spectrum image of said face of said subject; and, said calculate said plurality of health metrics of said subject comprises identify under-eye regions of said ultraviolet spectrum image;

calculate a Fourier transform of said under-eye regions of said ultraviolet spectrum image;

calculate a difference between said Fourier transform of said under-eye regions and a reference Fourier transform based on one or more of said plurality of reference population distributions;

calculate said chromophores based on said difference.

13. The system of claim 1, wherein said plurality of health metrics of said subject comprise pallor;

temperature;

sweat; and, chromophores.

14. A hyperspectral facial analysis system and method for personalized health scoring comprising:

a plurality of imaging sensors configured to capture images in a plurality of electromagnetic spectral bands, wherein said plurality of electromagnetic spectral bands comprises a visible spectrum band comprising 540 nanometers;

an infrared spectrum band comprising 700 nanometers; and an ultraviolet spectrum band comprising 300 nanometers; and, a processor coupled to said plurality of imaging sensors and configured to receive a multiplicity of person images from said plurality of imaging sensors, wherein each person image of said multiplicity of person images comprises a face of a corresponding person of a reference population;

identify under-eye regions of said each person image, wherein said under-eye regions of said each person image comprise lower periorbital regions of said face of said corresponding person;

analyze said under-eye regions corresponding to said multiplicity of person images to form a plurality of reference population distributions;

receive a plurality of subject images from said plurality of imaging sensors, wherein each subject image of said plurality of subject images comprises a face of a subject;

identify under-eye regions of said each subject image, wherein said under-eye regions of said each subject image comprise lower periorbital regions of said face of said subject;

calculate a plurality of health metrics of said subject based on comparisons of only said under-eye regions of said each subject image to one or more of said plurality of reference population distributions, wherein said plurality of health metrics comprise pallor;

temperature;

sweat; and chromophores; and, calculate a health score of said subject based on said plurality of health metrics of said subject.

15. The system of claim 14, wherein said plurality of subject images comprise a visible spectrum image of said face of said subject; and, said calculate said plurality of health metrics of said subject comprises
identify under-eye regions of said visible spectrum image;
calculate a hue image of said under-eye regions of said visible spectrum image;
calculate a saturation image of said under-eye regions of said visible spectrum image;
calculate a median hue of said hue image;
calculate a median saturation of said saturation image;
calculate a relative hue based on a comparison of said median hue to said one or more of said plurality of reference population distributions;
calculate a relative saturation based on a comparison of said median saturation to said one or more of said plurality of reference population distributions; and,
calculate said pallor based on said relative hue and said relative saturation.

16. The system of claim 14, wherein
said plurality of subject images comprise an infrared spectrum image of said face of said subject; and,
said calculate said plurality of health metrics of said subject comprises
identify under-eye regions of said infrared spectrum image;
calculate a median pixel value of said under-eye regions of said infrared spectrum image;
calculate a relative pixel value based on a comparison of said median pixel value to said one or more of said plurality of reference population distributions; and,
calculate said temperature based on said relative pixel value.

17. The system of claim 14, wherein
said plurality of subject images comprise a pair of visible spectrum images of said face of said subject with different polarizations; and,
said calculate said plurality of health metrics of said subject comprises
identify under-eye regions of said pair of visible spectrum images;
identify high-luminance, low-saturation pixels of said under-eye regions of said pair of visible spectrum images;
calculate a difference between
said high-luminance, low-saturation pixels of under-eye regions of a first image of said pair of visible spectrum images, and
said high-luminance, low-saturation pixels of under-eye regions of a second image of said pair of visible spectrum images;
calculate a relative difference based on a comparison of said difference to said one or more of said plurality of reference population distributions;
calculate said sweat based on said relative difference.

18. The system of claim 14, wherein
said plurality of subject images comprise an ultraviolet spectrum image of said face of said subject; and,
said calculate said plurality of health metrics of said subject comprises
identify under-eye regions of said ultraviolet spectrum image;
calculate a Fourier transform of said under-eye regions of said ultraviolet spectrum image;
calculate a difference between said Fourier transform of said under-eye regions and a reference Fourier transform based on one or more of said plurality of reference population distributions;
calculate said chromophores based on said difference.

* * * * *